United States Patent [19]

Bennett, Jr. et al.

[11] Patent Number: 4,503,272

[45] Date of Patent: Mar. 5, 1985

[54] PROCESS FOR MAKING ORTHO-ALKYLATED PHENOLS

[75] Inventors: James G. Bennett, Jr., Glenmont, N.Y.; Freddie L. Tungate, Georgetown, Ind.; John J. Kokoszka, Delmar, N.Y.

[73] Assignee: General Electric Company, Selkirk, N.Y.

[21] Appl. No.: 496,696

[22] Filed: May 20, 1983

[51] Int. Cl.³ ................. C07C 37/16; C07C 39/06
[52] U.S. Cl. .................... 568/804; 502/174; 502/324
[58] Field of Search ............ 568/804, 794; 252/471, 252/475

[56] References Cited

U.S. PATENT DOCUMENTS 3,873,628  3/1976  Van Sorge ..................... 568/804
3,972,836  8/1976  Van Sorge ..................... 568/804
3,974,229  8/1976  Van Sorge ..................... 568/804
4,041,085  8/1977  Frabetti ......................... 568/804
4,100,207  7/1978  Goodwin ........................ 568/804
4,227,023  10/1980 Kawamata et al. .............. 568/804

FOREIGN PATENT DOCUMENTS 2127083  12/1971  Fed. Rep. of Germany ...... 568/804

Primary Examiner—Werren B. Lone

[57] ABSTRACT

A process for making ortho-alkylated phenols by reacting in the vapor phase an alkyl alcohol and a phenolic compound in the presence of an alkylation catalyst, said catalyst provided by a calcination residue of mixture comprising a magnesium-containing material and manganese hydroxide formed as a precipitate by bringing together an aqueous solution of a manganese salt and an aqueous solution of ammonium hydroxide in the presence of said magnesium-containing material.

15 Claims, 1 Drawing Figure

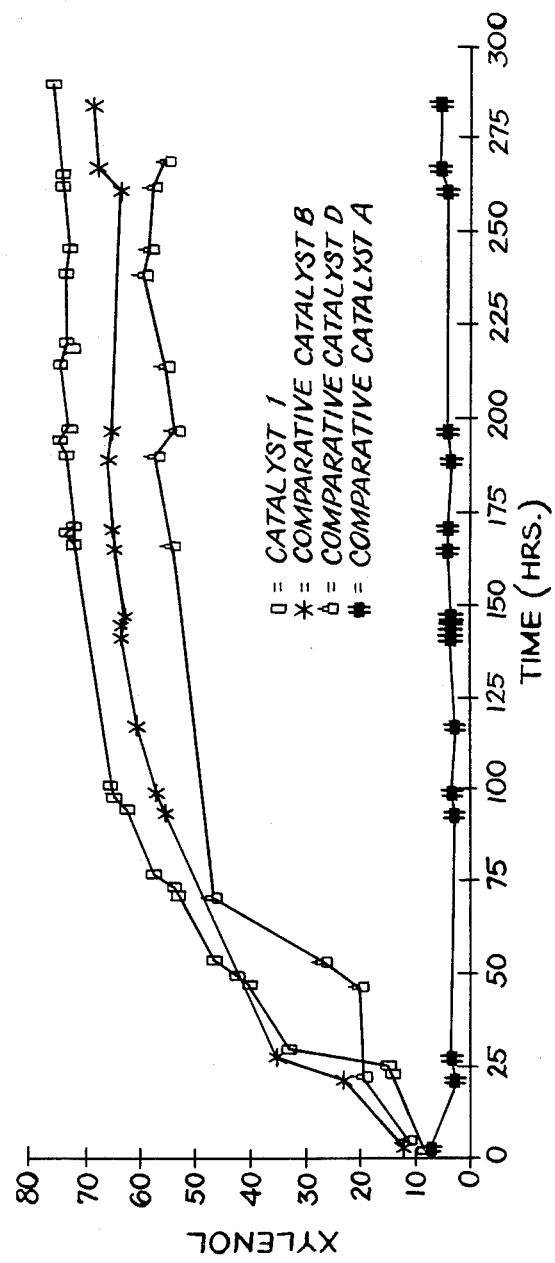

PROCESS FOR MAKING ORTHO-ALKYLATED PHENOLS

BACKGROUND OF THE INVENTION

1. Field of the Invention

Catalysts provided by mixtures of certain magnesium-containing compounds and manganese-containing compounds are well known. There is herein described a catalyst of particular interest which is derived from a novel precursor made by depositing manganese hydroxide on a magnesium-compound matrix and which is particularly effective in a process for ortho-alkylating phenolic compounds.

2. State of the Art

In U.S. Pat. No. 3,873,628 of Van Sorge, an ortho-alkylation catalyst is prepared by mixing magnesium oxide with aqueous manganese sulfate, heating the mixture till dry and then calcining the dried mixture. In U.S. Pat. No. 3,972,836 of Van Sorge, an ortho-alkylation catalyst is prepared by dry blending magnesium oxide and manganese oxides, wherein the manganese hydroxides may be precipitated from an aqueous solution of manganese sulfate and potassium hydroxide. In U.S. Pat. No. 4,041,805 of Frabetti, an ortho-alkylation catalyst is described which comprises a mixture of magnesium oxide and magnesium oxide. The magnesium oxide component is derived by thermal decomposition of magnesium carbonate, basic magnesium carbonate or magnesium hydroxide. The manganese oxide component is derived as a precipitate from a solution of manganese sulfate and potassium hydroxide.

All of the catalyst materials described in the aforementioned patents suffer disadvantages either in catalyst preparatory methods or in use of the catalyst in an ortho-alkylation process. For example, the Van Sorge '628 catalyst containing sulfate anion generates significant amounts of mercapto-containing compounds which may be highly offensive to the environment. The later Van Sorge '836 patent specifically teaches that the catalyst materials must be washed repeatedly with an alkaline solution in order to remove both sulfate and potassium ions.

BRIEF DESCRIPTION OF THE DRAWING

FIG. 1 is a graph plot of weight percent yield of 2,6-xylenol over a period of about 300 hours in an ortho-alkylation process using a catalyst and process of the present invention as compared to prior art catalyst materials and processes.

DESCRIPTION OF THE INVENTION

A catalyst precursor is provided by a mixture of a magnesium-containing material and manganese hydroxide formed as a precipitate by bringing together an aqueous solution of a manganese salt and an aqueous solution of ammonium hydroxide in the presence of the magnesium-containing material. Calcining this mixture provides a catalyst useful in the process of ortho-alkylation of phenolic compounds. Such catalyst is especially useful in the production of 2,6-xylenol.

The magnesium-containing material which constitutes a matrix upon which manganese hydroxide is deposited, may be provided by magnesium carbonate, basic magnesium carbonate, magnesium hydroxide, or a mixture of two or more of these magnesium-containing compounds. The term "basic magnesium carbonate" refers to a material represented by the formula $$xMgCO_3 \cdot Mg(OH)_2 \cdot xH_2O$$

wherein each "x" independently may be a number average from about 3 to about 5.

The manganese hydroxide component of the catalyst precursor is formed as a precipitate by bringing together an aqueous solution of a manganese salt and an aqueous solution of ammonium hydroxide. These aqueous solutions may be brought together in the presence of a slurry of magnesium compounds in water. Suitable manganese salts include manganese nitrate sulfate or acetate. It is contemplated that manganese chloride, manganese bromide and the like would also be suitable.

In preparing the catalyst precursor, a water-soluble manganese compound is added as a solution in water to an aqueous slurry or suspension of the magnesium compound, to which is then added the ammonium hydroxide.

The magnesium compound is preferably "basic" magnesium carbonate, especially in finely divided particulate form. Any magnesium carbonate will suffice, however.

The reaction mixture will preferably contain the magnesium and manganese compounds in amounts sufficient to provide approximately 0.02 to 0.25 moles of manganese per mole of magnesium in the finally prepared catalyst.

Stirring may be and preferably is carried out at room temperature, e.g., about 25° C. Although it is unnecessary, the reaction mixture can be heated above room temperature. The period for the stirring step may be brief, with times of from 10 to 30 minutes, in general, being sufficient to accomplish deposition of at least a portion of the manganese in the form of manganous hydroxide onto the magnesium compound.

After the manganese hydroxide is precipitated onto the magnesium compound, at least a portion of the compound with the manganese hydroxide deposited thereon is separated from the balance of the reaction mixture by any suitable separation procedure, such as, by filtration, centrifuging, etc. Centrifuging is preferred for large-scale production. However, good results can be obtained using almost any known separation procedure.

It should again be noted that after this initial separation of the catalyst from its reaction mixture, it can be dried directly without the necessity for washing, which is required when the catalyst is prepared in the presence of caustics such as sodium hydroxide in accordance with the prior art. Lack of necessity for washing or reslurrying one or more times is a significant advantage of the present invention.

Drying of the separated magnesium compound having manganese hydroxide deposited thereon may be effected in any suitable manner, using hot air, vacuum, combination thereof, etc. Preferably, drying is effected at temperatures below 200° F. to a sufficiently dry state (e.g. 2% volatiles or less; preferably 1% volatiles or less) such that the material can be pulverized to a substantially free-flowing particulate form.

After drying, the dried separated portion is formed into finely divided particulate form, as by grinding or the like, of preferably sufficiently small size to pass through a 16 to 20 mesh screen.

Thereafter, the particles are shaped to the desired physical form using any suitable shaping method and device. For example, the particles may be formed into tablets using a tabletting press and well-known tabletting procedures. The shaped particles may be in the form of pellets, cylinders, tablets or any other shape known in the art.

After shaping and before use, the particles are calcined. Calcining is effected preferably at temperatures in the range between 250° and 500° C. This is done most advantageously in situ, that is, in the reactor in which the catalyst is to be employed to catalyze ortho-alkylation of a phenol. It is to be understood, however, that the catalyst precursor composition of the present method can be calcined in any suitable manner, thereby providing an effective ortho-alkylation catalyst. It is contemplated that other calcining methods would include calcining under vacuum, under feed or under an inert atmosphere.

If desired, shaping aids and/or binders may also be employed in preparing the catalyst. In one such procedure, a small amount, e.g. 0.5%, of graphite is added to the catalyst particles prior to tabletting. In another procedure, a polyphenylene oxide, such as described in Hay, U.S. Pat. Nos. 3,306,874 and 3,306,875, is compounded with the particles in amounts of up to 20% by weight as a binding agent. It is also contemplated that polyphenylene oxide resin copolymers may also be utilized as an effective binder material. In general well known water soluble and insoluble binder materials may be utilized with the precursor and catalyst materials of the present invention.

The catalyst may be employed to effect or facilitate the ortho-alkylation of phenolic compounds such as those having the formula:

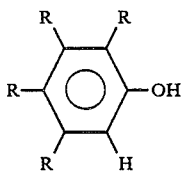

where each R, independently, is a monovalent substituent selected from the group consisting of hydrogen, alkyl, e.g., $C_1$–$C_{12}$ alkyl, phenyl and alkyl-substituted phenyl, e.g., $C_1$–$C_{12}$ alkyl-substituted phenyl.

In carrying out an alkylation using the catalyst of the invention, any one or a mixture of such phenols is vaporized and passed through a reactor heated to a temperature of at least 400° C., and preferably 400° to 460° C. and containing the magnesium carbonate-manganese hydroxide catalyst.

For best results, it is advisable to use at least one mole of the alkyl alcohol, and preferably from 1 to 3 moles, for each ortho position on the phenol to be alkylated. For example, if phenol, which has two ortho hydrogens per molecule, is to be methylated to produce a maximum yield of 2,6-xylenol, it is desirable to use two to six moles of methanol for each mole of phenol, with higher yields being obtained with higher ratios of methanol to phenol.

The vapors issuing from the reactor are condensed and the products are separated by conventional methods such as crystallization, distillation, etc. The reaction proceeds at atmospheric pressure, but pressures above or below can be used.

The desired ortho-alkylated end product is recovered in good yield. Selectivity favoring ortho alkylation over meta and para alkylation is good.

The following examples are illustrative of the invention and are not construed to be limiting. These include comparisons with other catalysts.

EXAMPLE I

The following example illustrates preparation and use of a catalyst precursor in accordance with the invention:

In a vessel equipped with a thermometer and stirring means, 906 g magnesium carbonate (Fisher Chemical, Lab Grade, Lot 790876) was stirred into 4000 ml distilled water to form a slurry. Then 80.0 g of a 50 wt. % manganese nitrate aqueous solution (Fisher Chemical, Lot 781811) was diluted with distilled water to a 1000 ml volume, and this diluted solution at room temperature was added dropwise to the slurry over a 245-second period with mixing of the slurry. Then 60.0 g of a 29.3 wt. % ammonium hydroxide aqueous solution (J. T. Baker Chemical Co., Analyzed Reagent Grade) was poured rapidly into the slurry. Stirring was continued for about 10 minutes. The slurry solids were then separated from the mother liquor by vacuum filtration. The resulting filter cake was placed in a pan and dried overnight in a cavuum oven at 104° C. The dried cake was then ground through a #25 mesh screen and the resulting powder was blended in a jar mill 15 minutes with poly(2,6-dimethyl-1,4-phenylene ether) resin (General Electric Co.) in a ratio of catalyst precursor-to-resin of 90:10. This powder was then compressed on a press into tablets 3/16 inch (0.48 cm) in diameter and ⅛ inch (0.32 cm) in length.

The Reactor

The catalyst prepared from the catalyst precursor described above was evaluated in a reactor which is described as follows:

The reactor consists of two ¾ inch (1.91 cm) inside diameter tubes. The feed, a solution of alcohol, water and phenol compound, is fed from a reservoir through a metering pump into the first of the two ¾ inch (1.91 cm) (I.D.) tubes, which functions as a vertical vaporizer. The tube is 15 inches (38.1 cm) in length and is partially immersed to a depth of 8 inches (20.3 cm) in a fused salt bath. The vapors from the vaporizer are fed to the second ¾ inch (1.91 cm) (I.D.) tube, which functions as a vertical reactor, through a 2 inch (5.1 cm) length of stainless steel tubing located 5 inches (12.7 cm) above the bottom of the vaporizer and connected to the reactor tube 14 inches (35.6 cm) up from its bottom. The reactor tube is 24 inches (60.96 cm) long and is immersed in the fused salt bath to a depth of 17 inches (43.2 cm).

The inlet tube of the reactor coming from the vaporizer also passes through the fused salt bath and serves as a preheater for the vapor issuing from the vaporizer to bring the vapor up to the temperature of the reactor tube.

The second ¾ inch (1.91 cm) (I.D.) tube (i.e., the reactor tube) is filled to a depth of 2 inches with glass beads which serve as support for the catalyst bed, and to a depth of 12 inches (30.5 cm) with 110 ml. of catalyst. The vapors from the vaporizer are fed to the top of the catalyst bed and product vapors leave the bottom of the reactor tube through a ⅜ inch (0.95 cm) (I.D.) stainless steel outlet tube. The product vapors are led to a watercooled condenser and receiver where they are liquefied and recovered. The non-condensibles are fed to an off-gas meter where they can be measured.

Ortho-Alkylation Process

The catalyst was evaluated in an ortho-alkylation process as follows.

The reactor was charged with 110 ml. of the catalyst, capped and placed in a 370° C. salt bath and nitrogen gas was blown over the catalyst bed at a rate of 2 standard cubic feet per hour (SCFH). After 15 minutes the phenolic feed was started. This consisted of 4:1 methanol to phenolics, with the phenolics being 60:40 phenol:ortho-cresol and 20% water. The feed rate was 215 ml/hour, equivalent to a liquid hourly space velocity (LHSV) of 1.95. This rate was maintained for the duration of the run. The pressure was atmospheric.

Using this catalyst a temperature program was followed to maintain the desired rate of conversion of the feed to the end product. After the feed was established at 370° C., the temperature was raised to 445° C. which was reached in 1.5 to 2.5 hours. Listed below are the approximate time and temperature changes over the duration of the 506 hour run.

| Time, hrs. | Temp., °C. |
|---|---|
| 0 | 370 |
| 0.5–8 | 445 |
| 8–26 | 450 |
| 26–78 | 455 |
| 78–506 | 458 |

The phenolic distribution resulting during the procedure is summarized in Table 1, with off gas stated in SCFH and the other materials in weight percent.

TABLE 1

| Time, /hrs. | Temp. °C. | Off Gas | Phenol | o-Cresol | 2,6 | 2,4,6 |
|---|---|---|---|---|---|---|
| 197 | 458 | 0.58 | 1.8 | 21.1 | 72.8 | 3.8 |
| 239 | 458 | 0.59 | 2.3 | 20.0 | 76.4 | 4.2 |
| 506 | 458 | 0.40 | 6.6 | 30.3 | 59.8 | 2.9 |
| TWA | 457 | 0.47 | 4.7 | 27.0 | 64.1 | 3.6 |

COMPARATIVE EXAMPLE A

The following example illustrates preparation and use of a prior art catalyst precursor using caustic media:

In a vessel equipped with a thermometer and stirring means, 519 g magnesium carbonate (Merck Chemicals, commercial Lot AMQ) was stirred into 2000 ml distilled water) to form a slurry. Then 40.0 g of a 50 wt. % manganese nitrate aqueous solution (Fisher Chemical, Lot 781811) was diluted with distilled water to a 500 ml volume, and this diluted solution at room temperature was added dropwise to the slurry over a 245-second period with mixing of the slurry. Then 10.8/g of a 50 wt. % sodium hydroxide aqueous solution (Mallinkcrodt, Lot CTA#7705) was diluted with distilled water to a 500 ml volume, and this diluted caustic solution at room temperature was added to the slurry over a 245-second period with mixing of the slurry. Stirring of the slurry was continued for one hour at room temperature. The slurry solids were then separated from the mother liquor by vacuum filtration with a medium-fritted filter. Then without washing, the resulting filter cake was placed in a pan and dried overnight in a vacuum oven at 103° C. The dried cake was then ground through a 25 mesh screen, U.S. Standard Sieve, and the resulting powder was blended in a jar mill for 15 minutes with poly(2,6-dimethyl-1,4-phenylene ether) resin (General Electric Co.) in a ratio of catalyst precursor-to-resin of 90:10. This fluffy, powdery material was then compressed for a first time on a press to form tablets which, in turn, were ground and sifted again through a #25 mesh screen to form a denser powder. The denser powder was then compressed into cylindrical tablets 3/16 inch (0.48 cm) in diameter and ⅛ inch (0.32 cm) in length.

The catalyst was evaluated using the reactor described above. One hundred and ten milliliters of the catalyst was charged. The reactor was capped and placed in a 370° C. salt bath. Nitrogen gas was blown over the catalyst bed a rate of 2 SCFH. After 15 minutes of nitrogen flow the phenolic feed stream was started. The feed has the same composition as in Example 1. The feed rate was 228 ml/hour, equivalent to a LHSV of 2.07, which was maintained throughout the run. Listed below are the approximate time-temperature changes over the course of the 285 hour run.

| Time, Hrs. | Temp. °C. |
|---|---|
| 0 | 370 |
| 0.5–20 | 445 |
| 20–25 | 450 |
| 25–261 | 455 |
| 261–285 | 460 |

The phenolic distribution for the run is summarized in Table 2, with off gas stated in SCFH and other materials in weight percent.

TABLE 2

| Time, hrs. | Temp. °C. | Off Gas | Phenol | o-Cresol | 2,6 | 2,4,6 |
|---|---|---|---|---|---|---|
| 189 | 455 | 0.11 | 42.9 | 52.5 | 3.8 | 0.3 |
| 285 | 460 | 0.16 | 38.8 | 55.0 | 5.4 | 0.3 |
| TWA | 455 | 0.11 | 43.3 | 51.6 | 4.0 | 0.7 |

COMPARATIVE EXAMPLE B

The following example illustrates preparation and use of a catalyst precursor using caustic media, in which preparation a washing step is used to remove deleterious cations:

In accordance with the procedures of Comparative Example A, a wet filter cake was formed by using vacuum filtration to separate slurry solids from the mother liquor. Then, as a washing step, 1500 ml distilled water was poured onto the filter cake, the cake was vigorously mixed to form a slurry, and then the slurry was vacuum filtered. The washing step was repeated four times for a total of five washing steps. Then the wet cake was treated in accordance with the procedures of Comparative Example A to form tablets 3/16 inch (0.48 cm) in diameter and ⅛ inch (0.32 cm) in length. Amounts are in units as previously stated.

TABLE 3

| Time, hrs. | Temp. °C. | Off Gas | Phenol | o-Cresol | 2,6 | 2,4,6 |
|---|---|---|---|---|---|---|
| 189 | 455 | .455 | 3.26 | 27.38 | 65.80 | 3.14 |
| 285 | 460 | .580 | 3.40 | 25.19 | 67.83 | 3.22 |
| TWA | 455 | .372 | 6.66 | 33.25 | 55.68 | 4.22 |

COMPARATIVE EXAMPLE C

A catalyst was prepared by stirring 453.2 grams of MgCO₃, Fisher lab grade, into 2000 ml. of distilled water. 40.0 grams of Mn(NO₃)₂ were added to the slurry from a separatory funnel over a period of 4 minutes. Then 10.8 grams of NaOH, 58%, diluted to 500 ml. with distilled water, were added over 4 minutes. The slurry was stirred for one hour at room temperature, then poured onto a 3000 ml. medium fritted funnel and vacuum filtered. After the filtration, 1500 ml. of distilled water were poured onto the wet filter cake. The cake was resuspended by homogenizing in water, then vacuum filtered again. The reslurrying and filtration were repeated four more times. Then a last reslurry was done using 250 ml. of acetone instead of water. The filter cake was dried overnight under vacuum at 120° C., then ground with a mortar and pestle to a fine powder. The powder was blended with PPO on a jar mill for 15 minutes to make a 90:10 catalyst: PPO blend, which was thereafter tableted to 1/16 inch ×3/16 inch size (0.16×0.48 cm).

The catalyst was used in an alkylation procedure as described in comparative examples A and B, with the approximate time and temperature changes noted below. Total duration of the run was 506 hours. The results are summarized in Table 4. Amounts are in units as stated previously.

| Time, hrs. | Temp., °C. |
|---|---|
| 0 | 370 |
| 0.5–8 | 445 |
| 8–26 | 450 |
| 26–78 | 455 |
| 78–506 | 458 |

TABLE 4

| Time, hrs. | Temp. °C. | Off Gas | Phenol | o-Cresol | 2,6 | 2,4,6 |
|---|---|---|---|---|---|---|
| 197 | 458 | .660 | 1.47 | 18.71 | 74.70 | 4.69 |
| 239 | 458 | .700 | 1.77 | 18.71 | 74.57 | 4.65 |
| 506 | 458 | .470 | 4.16 | 24.58 | 66.44 | 4.48 |
| TWA | 457 | .572 | 3.43 | 23.31 | 67.90 | 4.60 |

The foregoing examples are summarized in Table 5 which offers a convenient means of comparing the various procedures. It can be seen that the catalyst of the present invention provides comparable results in an ortho-alkylation process when compared to Comparative Example C which required 5 washing steps. The catalyst for Example I offered considerably improved performance over Comparative Examples A and B.

TABLE 5
EXAMPLE SUMMARY

| Example | No. of Washes | Hrs. | Temp. | Off Gas | Phenol | o-Cresol | 2,6 | 2,4,6 |
|---|---|---|---|---|---|---|---|---|
| A* | MgCO₃/PPO | 189 | 455 | .110 | 42.86 | 52.53 | 3.82 | .54 |
|    | NaOH/0 Washes | 285 | 460 | .160 | 38.77 | 54.94 | 5.40 | .60 |
|    |  | TWA | 455 | .110 | 43.34 | 51.56 | 4.02 | .68 |
| B* | MgCO₃/PPO | 189 | 450 | .455 | 3.26 | 27.38 | 65.80 | 3.55 |
|    | NaOH/5 Washes | 285 | 460 | .580 | 3.40 | 25.19 | 67.83 | 3.59 |
|    |  | TWA | 455 | .372 | 6.66 | 33.25 | 55.68 | 4.33 |
| C* | MgCO₃/Mn(NO₃)₂ | 197 | 458 | .660 | 1.47 | 18.71 | 74.70 | 4.69 |
|    | NaOH/5 Wash | 239 | 458 | .799 | 1.77 | 18.71 | 74.57 | 4.65 |
|    |  | TWA | 457 | .572 | 3.43 | 23.31 | 67.90 | 4.60 |
| 1  | MgCO₃/Mn(NO₃)₂ | 197 | 458 | .575 | 1.84 | 21.10 | 72.80 | 3.78 |
|    | NH₄OH/0 Wash | 239 | 458 | .590 | 2.28 | 19.96 | 76.43 | 4.16 |
|    |  | TWA | 457 | .4723 | 4.65 | 26.98 | 64.07 | 3.63 |

*comparative purposes

FIG. 1 depicts comparative results for several ortho-alkylation processes, where percent yield of 2,6-xylenol is measured over a period of time up to about 300 hours.

In the figure, the catalyst depicted by line I was the catalyst prepared in accordance with Example I above. Lines A and B depict the catalysts of Comparative Examples A and B, respectively. The catalytic process depicted by line D used a catalyst prepared in accordance with Example 3 of U.S. Pat. No. 3,972,836 of Van Sorge, run at 25 psi.

The effectiveness of the catalytic process of the present invention can be seen with reference to line I. The catalyst used for the process run described by line I provided selectivity for 2,6-xylenol to a far greater degree than that shown for the prior art processes represented by lines A,B, and D. Indeed, for a majority of the process run, catalyst I provided yields of 2,6-xylenol in excess of 70 percent of weight. The difference in activity between the catalysts can be readily seen.

Furthermore, the difference in activity between catalysts I and D is obtained despite the fact that the process of catalyst I was run at atmospheric pressure and D was run at 25 psi which would normally be expected to increase the effectiveness of the catalyst.

Additionally, catalyst B required several washing steps to remove deleterious cations from the catalyst. Such washings were not required for the catalyst of process I. Comparative catalyst A also was not washed and its performance was markedly inferior to that of catalyst I.

It is therefore evident that the catalyst precursor composition of the present invention provides an efficient and improved means for catalyzing the ortho-alkylation of phenols.

The above mentioned patents are incorporated herein by reference. Other modifications and variations of the invention are possible in light of the above disclosure. Process conditions such as time, temperature, feed rations, rates, etc. may also be varied depending on particular requirements. It should be understood, therefore, that changes may be made in the particular embodiments described which are still within the full intended scope of the invention as defined the the appended claims.

What is claimed is:

1. In a process for making ortho-alkylated phenols by reacting in the vapor phase a phenolic compound and an alcohol containing up to about 16 carbon atoms in the presence of an alkylation catalyst, the improvement comprising catalyzing said reaction with a catalyst provided by a calcination residue of a mixture comprising a magnesium-containing material selected from the group consisting of magnesium carbonate, basic magnesium carbonate, or magnesium hydroxide; and a manganese hydroxide formed as as precipitate by bringing together an aqueous solution of a manganese salt and an aqueous solution of ammonium hydroxide in the presence of said magnesium-containing material wherein said mixture is characterized by a mole ratio of manganese to magnesium in a range from about 0.02 to 1.0 to about 0.25 to 1.0 and said ortho-alkylation process takes place at a temperature in a range from about 300° C. to about 500° C.

2. The process of claim 1 wherein said alkyl alcohol is a branched or linear saturated alcohol having up to about 16 carbon atoms.

3. The process of claim 1 wherein said phenolic compound is represented by the formula

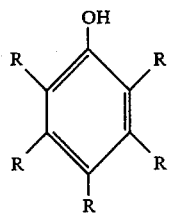

wherein R is, independently, a monovalent substituent selected from the group consisting of hydrogen, alkyl, phenyl and alkyl-substituted phenyl.

4. The process of claim 1 wherein said magnesium-containing compound is provided by one or more of magnesium carbonate, basic magnesium carbonate, or magnesium hydroxide.

5. The process of claim 1 wherein said mixture is characterized by a mole ratio of manganese-to-magnesium in a range from about 0.02-to-one to about 0.25-to-one.

6. The process of claim 1 wherein said vapor-phase mixture comprises methanol as the alkyl alcohol and the phenolic compound is provided by a mixture of phenol and ortho-cresol, with methanol present in the vapor-phase mixture in an amount in a range from about two to about six moles of methanol for each mole of phenolic compound, with phenol constituting at least about 50 mole percent of the phenolic compounds.

7. The process of claim 1 wherein the step of reacting an alkyl alcohol with a phenolic compound takes place at a temperature in a range from about 300° C. to about 500° C.

8. The process of claim 1 wherein the step of reacting an alkyl alcohol with a phenolic compound taken place under a pressure of about one atmosphere.

9. The process of claim 1 wherein the step of reacting an alkyl alcohol with a phenolic compound takes place under a pressure greater than one atmosphere.

10. A process for making 2,6-xylenol from a feed mixture comprising methanol, phenol and ortho-cresol, by passing the feed mixture in the vapor phase in contact with an alkylation catalyst, said alkylation catalyst provided by a calcination residue of a mixture of manganese hydroxide and basic magnesium carbonate, in which residue the mole ratio of manganese-to-magnesium is in a range from about 0.02-to-one to about 0.25-to-one.

11. The process of claim 9 wherein said feed mixture comprises from about 60 to about 90 mole percent methanol, from about 8 to about 20 mole percent phenol and from about 5 to about 15 mole percent ortho-cresol.

12. The process of claim 9 wherein the temperature of said alkylation catalyst is in a range from about 300° C. to about 500° C.

13. The process of claim 9 wherein the calcination residue is formed by calcining an essentially sodium-free mixture of manganese hydroxide and basic magnesium carbonate while passing the feed mixture through said blend.

14. The process of claim 9 wherein said calcining takes place at a temperature in a range from about 300° C. to about 500° C.

15. The process of claim 1 wherein said manganese salt is selected from manganese nitrate, manganese sulfate, manganese acetate, manganese chloride, or manganese bromide, or mixtures of these.

* * * * *